(12) United States Patent
Zhang et al.

(10) Patent No.: US 6,586,638 B1
(45) Date of Patent: Jul. 1, 2003

(54) PROCESS FOR REMOVING AND RECOVERING OF PHENOLIC COMPOUNDS FROM AQUEOUS FLUIDS

(75) Inventors: Shengfu Zhang, London (GB); Jean-Pierre Arcangeli, Chatou (FR); Andrew Guy Livingston, London (GB); Andrew Timothy Boam, London (GB)

(73) Assignee: Membrane Extraction Technology Limited (GB)

( * ) Notice: Subject to any disclaimer, the term of this patent is extended or adjusted under 35 U.S.C. 154(b) by 0 days.

(21) Appl. No.: 10/110,946

(22) PCT Filed: Oct. 11, 2000

(86) PCT No.: PCT/GB00/03902

§ 371 (c)(1),
(2), (4) Date: Aug. 28, 2002

(87) PCT Pub. No.: WO01/28666

PCT Pub. Date: Apr. 26, 2001

(30) Foreign Application Priority Data

Oct. 19, 1999 (GB) .............................................. 9924724
Feb. 1, 2000 (GB) .............................................. 0002303

(51) Int. Cl.[7] .............................................. C07C 37/68
(52) U.S. Cl. ............. 568/749; 210/500.21; 210/500.23; 210/651; 568/755
(58) Field of Search ................................ 568/749, 755; 210/500.21, 500.23, 651

(56) References Cited

U.S. PATENT DOCUMENTS

| | | | |
|---|---|---|---|
| 3,931,000 A | | 1/1976 | Hamilton |
| 4,082,658 A | * | 4/1978 | Fritzsche |
| 4,597,875 A | | 7/1986 | Carr et al. |
| 4,806,245 A | * | 2/1989 | Boddeker |
| 4,987,273 A | * | 1/1991 | Bitter |
| 5,507,949 A | | 4/1996 | Ho |
| 5,552,053 A | | 9/1996 | Ho et al. |
| 5,585,004 A | | 12/1996 | Livingston |

FOREIGN PATENT DOCUMENTS

| | | |
|---|---|---|
| GB | 1480018 | 7/1977 |
| GB | 2 207 064 A | 1/1989 |

* cited by examiner

*Primary Examiner*—Michael L. Shippen
(74) *Attorney, Agent, or Firm*—Fay, Sharpe, Fagan, Minnich & McKee, LLP

(57) ABSTRACT

There is provided a process for removing and recovering one or more unassociated phenolic compounds dissolved in aqueous fluid, the process comprising the steps of: (a) transferring the one or more unassociated phenolic compounds from the aqueous fluid to an alkaline stripping solution, wherein transfer of the one or more unassociated phenolic compounds from the aqueous fluid to the alkaline stripping solution occurs across a membrane; wherein the membrane is a non porous, selectively permeable membrane; (b) regulating the volume of alkaline stripping solution employed relative to the volume of aqueous fluid treated so that the total phenolic compound concentration in the alkaline stripping solution, comprising the sum of the dissociated and unassociated phenolic compound concentrations, is above the solubility of the phenolic compounds in the acidified stripping solution of step (d); (c) regulating the pH of the alkaline stripping solution in contact with the membrane to a value at least 0.5 pH units above the acidic dissociation constant of the phenolic compound; (d) adjusting the pH of the phenolic compound containing alkaline stripping solution to a value below the alkaline dissociation constant of the phenolic compound and (e) separating the resulting phenolic compound rich phase and the alkaline stripping solution.

43 Claims, 7 Drawing Sheets

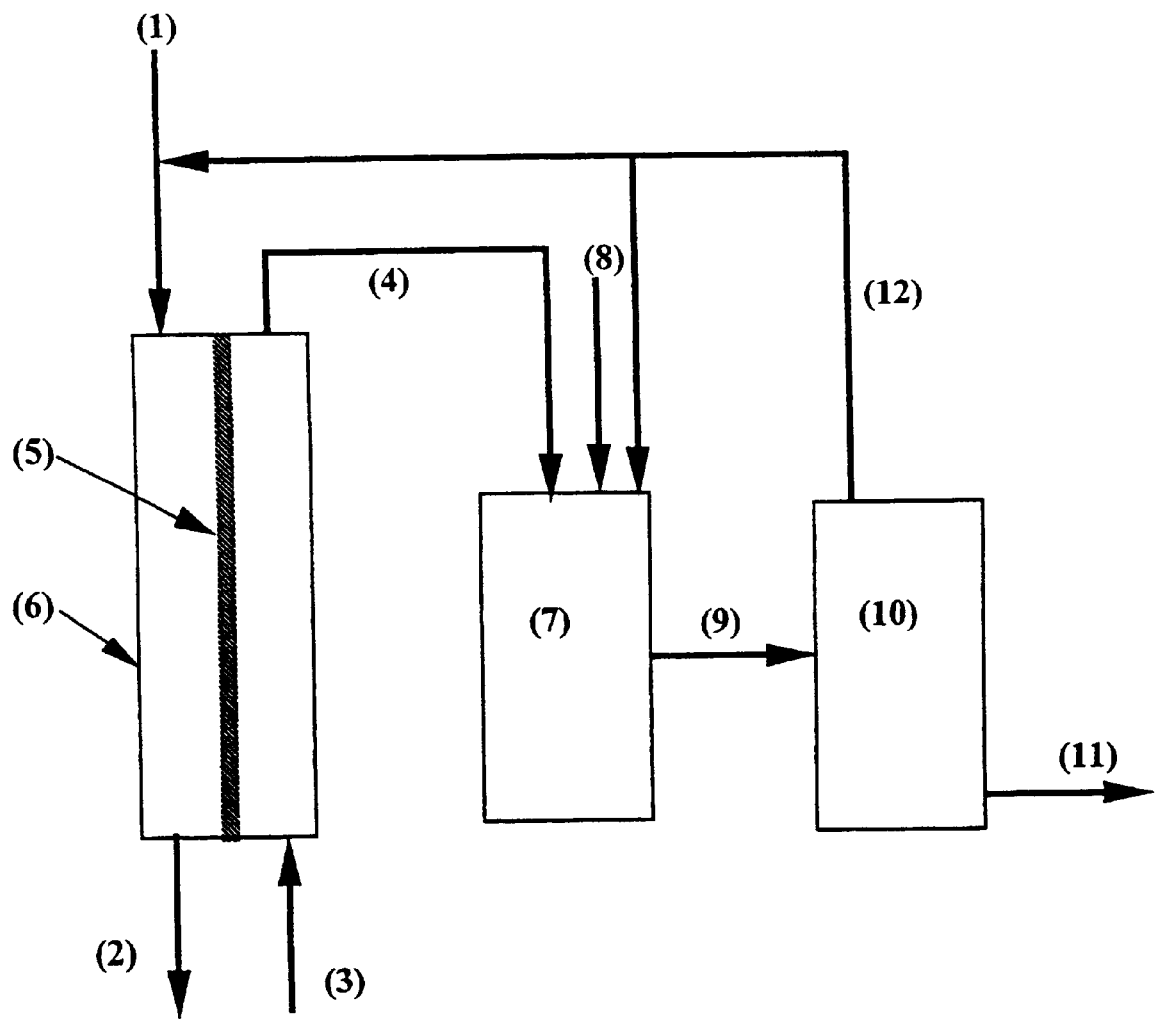
Figure 1 - Phenolic compound recovery process

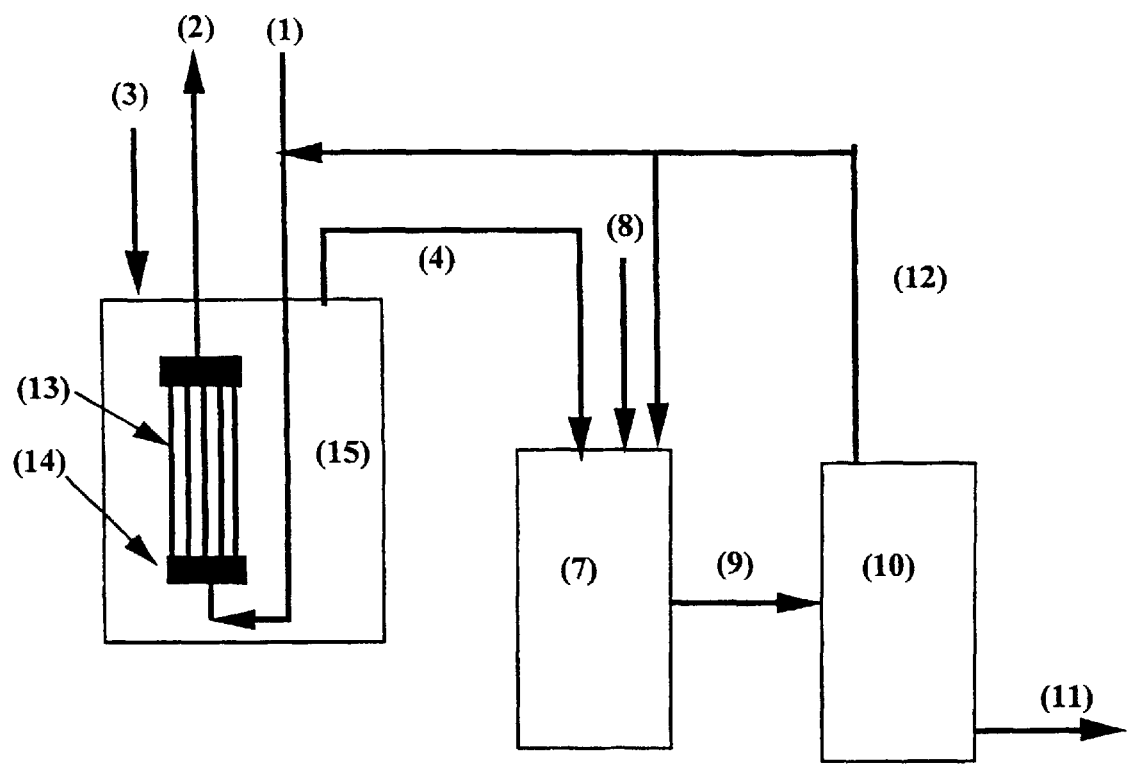
Figure 2- Phenolic compound recovery process with bundle of tubular membranes

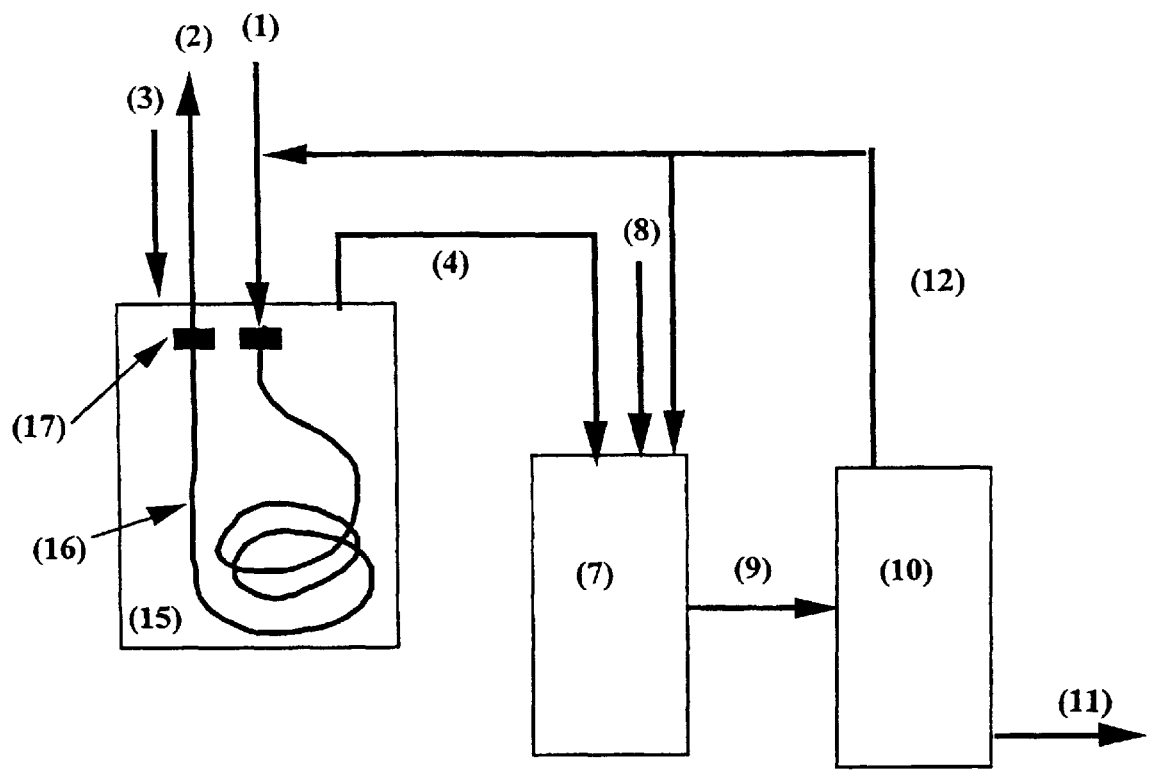
Figure 3- Phenolic compound recovery process with elastomeric tube membrane

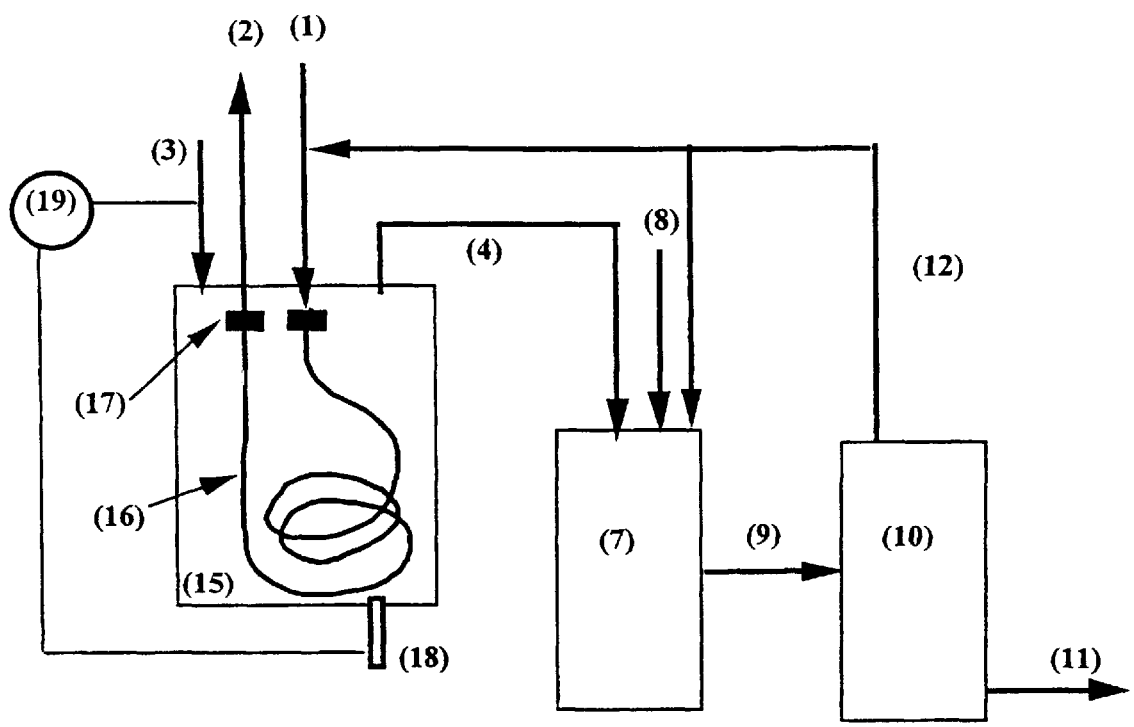
Figure 4- Phenolic compound recovery process with elastomeric tube membrane and pH control

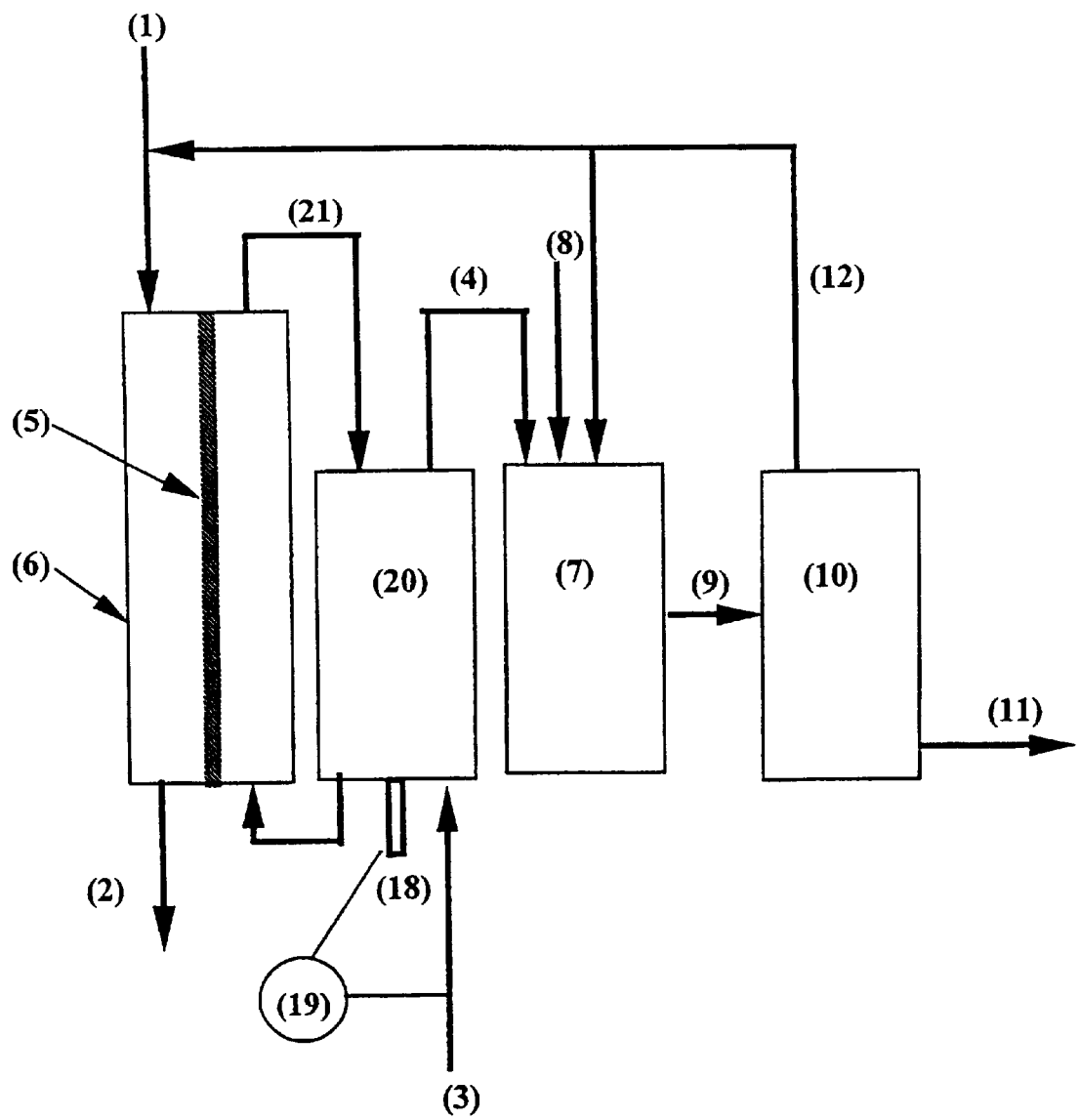
Figure 5 - Phenolic compound recovery process operated with a well mixed stripping solution recirculated at high rate to a remote membrane module.

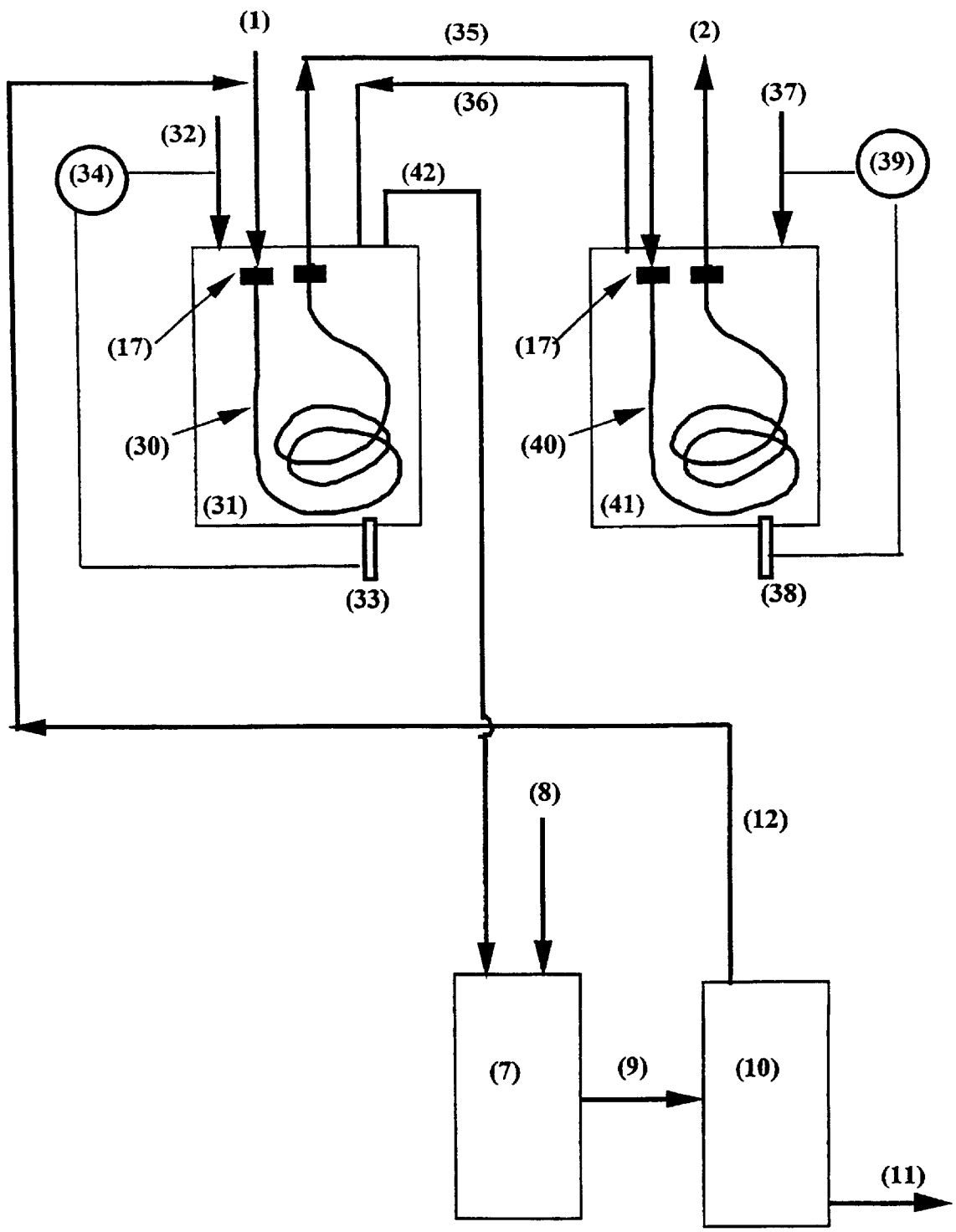
Figure 6 - Two stage phenolic compound recovery process

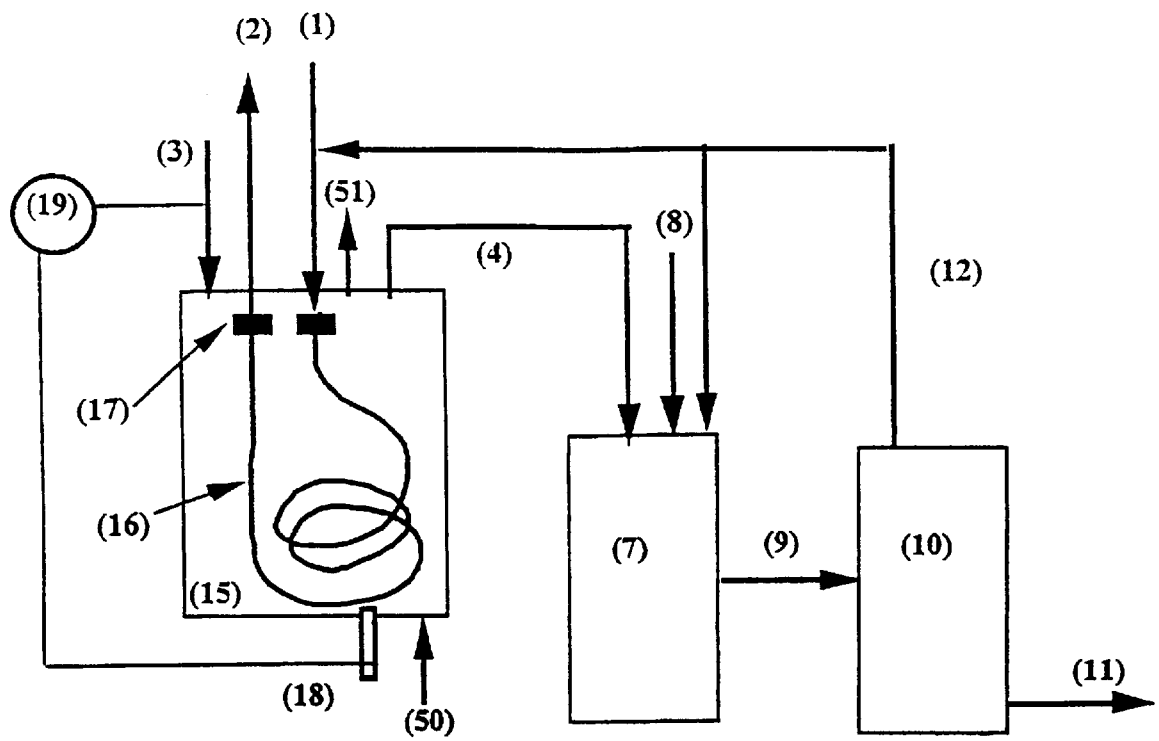
Figure 7- Phenolic compound recovery process with elastomeric tube membrane, pH control, and nitrogen sparging of the stripping solution.

PROCESS FOR REMOVING AND RECOVERING OF PHENOLIC COMPOUNDS FROM AQUEOUS FLUIDS

The present invention relates to a process for the removal and recovery of one or more phenolic compounds from an aqueous fluid. In particular the process comprises transferring the phenolic compounds from the aqueous fluid to an alkaline stripping solution across a non porous, selectively permeable membrane, adjusting the pH of the alkaline stripping solution and separating the resulting phenolic compound rich phase from the acidified stripping solution.

Many phenolic compounds, such as phenol, cresols, nitrophenols, chlorophenols, enter aqueous process streams in chemical processing. These molecules are in many cases toxic. Methods for removing toxic organic molecules from aqueous process streams are well known. Some of these methods use membranes.

Membrane solvent extraction using microporous membranes to provide a phase contacting between aqueous and organic streams is well known. For example Kiani, Bhave and Sirkar Journal of Membrane Science 20 (1984) pp 125–145 report the use of microporous membranes for immobilising solvent interfaces during solvent extraction. Toppings, Micheals and Peretti Journal of Membrane Science 75 (1992) pp 277–292 report using microporous polypropylene fibres to stabilise phase interfaces during extraction of nitrophenol from an aqueous solution into octanol. U.S. Pat. No. 5,512,180 describes a process wherein polypropylene glycol MW 4000 was used to extract nitrophenol in a microporous membrane contactor.

A continuing problem with membrane supported solvent extraction with microporous membranes is the breakthrough of one phase into the other due to pressure imbalances. To overcome this problem, various improvements have been suggested such as using composite membranes comprising a thin layer of non-porous organic-permeable polymer bound to a microporous membrane to avoid phase breakthrough, for example U.S. Pat. No. 4,960,520. However, in all of these processes a solvent phase containing the organic compound is produced which must then be disposed of or treated in some way.

Contacting two aqueous streams with opposite sides of a membrane to effect extraction of organic pollutants from one side to the other is also known in the art. Supported liquid membranes have been applied in this mode. For example U.S. Pat. No. 5,507,949 describes a process wherein the pores of a microporous hydrophobic membrane are filled with a hydrophobic polyamphiphilic oligomeric or polymeric liquid to allow mass transport of various organics across the membranes. In this application the driving force for extraction across the supported liquid membranes may be provided by a stripping solution. The driving force produced by a stripping solution may rely upon conversion of an organic acid to its corresponding salt using a basic stripping solution, or conversion of an organic base to its corresponding salt using an alkaline stripping solution. Biologically active stripping solutions may also be utilised, for example U.S. Pat. No. 4,988,443 to Michaels et al. discloses a method for contacting an aqueous waste stream containing organic toxicants with a nutrient-containing aqueous stream using hollow fibre membranes with water immiscible solvent filled pores. The two streams do not mix but the organic toxicants are transferred from the waste stream across the membrane to the nutrient stream. Microorganisms growing associated with the outside of the hollow fibres utilise the nutrients and organic toxicants as growth substrates which provides the driving force for continued transport.

In further applications non-porous membranes have been employed to effect extraction of organic molecules from one aqueous stream into another. U.S. Pat. No. 5,552,053 discloses solid polyamphiphilic polymer films used for keeping separate two aqueous phases, one being a waste stream and the other a stripping solution in which the organic pollutant can be concentrated by conversion into an ionised form at controlled pH.

In the above prior art, membranes are substantially rigid and are employed in shell and tube modules, in plate and frame modules, or in spiral wound modules. These modules are designed to generate good mass transfer and fluid distribution around all of the membrane surfaces.

In a few cases, tubular elastomeric non-porous homogeneous membranes for example silicone rubber (cross linked polydimethoxysiloxane) tubes have been disclosed. The tubular elastomeric membranes provide separation by allowing specific chemical species (for example, hydrophobic organic molecules such as benzene, toluene, or their derivatives) to preferentially dissolve in the membrane and permeate across the membrane by diffusion under the influence of a chemical activity driving force. For example, U.S. Pat. No. 5,585,004 to Livingston discloses a system of apparatus and method wherein a waste stream containing toxic organic compounds is fed to the inside of selectively permeable silicone rubber membrane tubes suspended in a bioreactor receptacle filled with a biologically active medium. The toxic organic compounds diffuse across the silicone rubber membrane and into the biologically active medium where they are destroyed by the microbial culture.

Further examples of the use of tubular elastomeric membranes are oxygenation of microbial systems (Cote et al, Journal of Membrane Science 1989 47 p107), and pervaporation (Raghunath and Hwang, Journal of Membrane Science 1992 65 p147). In the field of chemical analysis, silicone rubber membranes have been used to extract organics from aqueous streams prior to analysis (U.S. Pat. Nos. 4,715,217; 4,891,137).

The processing of organic-laden stripping solutions comprising organic acids in dissociated form in an aqueous solution is known with regard to nitrophenolic compounds recovery. For example, various processes are known in the art for disposing of stripping solutions containing nitrophenolic materials. These stripping solutions are generated as a by-product of nitration reactions. U.S. Pat. No. 4,597,875 discloses a process for removing the nitrophenolic materials from an alkaline stripping solution by treating the wastewater with an acid to lower its pH and convert the nitrophenolic compounds to a water insoluble solid material which is separated out of the wastewater and can be disposed of by incineration. U.S. Pat. No. 4,925,565 discloses a process in which the alkaline stripping solution is treated with acid to lower its pH, following which a substantially water insoluble solvent is used to extract the nitrophenolic compounds from the wastewater at elevated temperature. The solvent is recovered by distillation and the residue containing nitrophenolics can be incinerated. In variations on U.S. Pat. No. 4,925,565, the same inventors use differential control of the pH to recover specific nitrophenolic fractions by solvent extraction (U.S. Pat. No. 4,986,917) and precipitation (U.S. Pat. No. 4,986,920). However, the recovery of the nitrophenolic fraction is complicated by the fact that the nitrophenols form solid precipitates upon acidification of alkaline wastewaters containing ionised nitrophenolic compounds at concentrations above the saturation concentration of non-ionised nitrophenolic compounds in water.

In the prior art utilising membranes for organics removal, the temperature of operation with many membranes is limited to between 50–60° C., for example when using microporous polypropylene membranes.

The present invention addresses the problems of the prior art.

In one aspect the present invention provides a process for removing and recovering one or more unassociated phenolic compounds dissolved in aqueous fluid, the process comprising the steps of: (a) transferring the unassociated phenolic compound from the aqueous fluid to an alkaline stripping solution, wherein transfer of the unassociated phenolic compound from the aqueous fluid to the alkaline stripping solution occurs across a membrane; wherein the membrane is a non porous, selectively permeable membrane; (b) regulating the volume of alkaline stripping solution employed relative to the volume of aqueous fluid treated so that the total phenolic compound concentration in the alkaline stripping solution, comprising the sum of the dissociated and unassociated phenolic compound concentrations, is above the solubility of the phenolic compound in the acidified stripping solution of step (d); (c) regulating the pH of the alkaline stripping solution in contact with the membrane to a value at least 0.5 pH units above the acidic dissociation constant of the phenolic compound: (d) adjusting the pH of the phenolic compound containing alkaline stripping solution to a value below the acidic dissociation constant of the phenolic compound and (e) separating the resulting phenolic compound rich phase and the acidified stripping solution.

By the term "selectively permeable" it is meant a membrane which is permeable to the unassociated phenolic compound and which is impermeable to the dissociated phenolic compound.

By the term "phenolic compound rich phase" it is meant a liquid or solid phase which contains more than 40 wt % phenolic compound.

It will be appreciated that the term "phenolic compound" includes any compound of the formula R—OH wherein R is or comprises an aromatic group.

The present inventors have found that control of the pH in the alkaline stripping solution assists in the reducing of costs and in increasing the membrane lifetime.

In the present invention, phenolic compounds present in an aqueous fluid in unassociated form are recovered by means of membrane extraction across a membrane. The membrane contains at least one non porous, selectively permeable layer. The phenolic compounds pass into an alkaline stripping solution in which the phenolic compounds undergo dissociation. The alkaline stripping solution is then further processed by adjusting the pH downwards until the phenolic compounds re-associate and precipitate out of solution as phenolic compound rich liquids or solids.

A phenolic compound will undergo a dissociation reaction when the pH of the stripping solution is above the pKa of the phenolic compound where pKa is the acidity constant and is defined as follows (see for example "Organic Chemistry" third Edition by T. W. G. Solomns, John Wiley and Sons, p 680):

$$R\text{—}OH + H_2O \leftrightharpoons R\text{—}O^- + H_3O^+ \qquad (1)$$

$$pKa = \log_{10}\left(\frac{[RO^-][H_3O^+]}{[ROH]}\right) \qquad (2)$$

where R is an aromatic group containing organic structure.

The phenolic compound containing alkaline stripping solution is subsequently neutralised to acid pH and the phenolic compounds return to unassociated form and precipitate out of solution as organic liquids or solids. The organic liquids or solids are separated from the acidified stripping solution. The separated acidified stripping solution may contain saturation levels of unassociated phenolic compounds and may be cycled back to the aqueous fluid to undergo further stripping. In the present invention the extraction and alkaline stripping solution regeneration stages are integrated so that the streams leaving the process are phenolic compound rich organic liquid and treated aqueous waste respectively.

In step (b) the volume of alkaline stripping solution employed relative to the volume of aqueous fluid treated may be regulated so that the total phenolic compound concentration in the alkaline stripping solution, comprising the sum of the dissociated and unassociated phenolic compound concentrations, is not only above the solubility of the phenolic compound in the acidified stripping solution of step (d), but is also above the solubility of the phenolic compound in water. In an alternative the total phenolic compound concentration in the alkaline stripping solution is above the solubility of the phenolic compound in the acidified stripping solution of step (d), but is no greater than the solubility of the phenolic compound in water. The latter alternative is possible because the acidified stripping solution of step (d) may contain salts. When salts are present the solubility of the phenolic compound in the solution is reduced when compared to pure water.

Thus in one aspect the present invention may provide a process for removing and recovering one or more unassociated phenolic compounds dissolved in aqueous fluid the process comprising the steps of (a) transferring the unassociated phenolic compound from the aqueous fluid to an alkaline stripping solution, wherein transfer of the unassociated phenolic compound from the aqueous fluid to the alkaline stripping solution occurs across a membrane; wherein the membrane is a non porous, selectively permeable membrane; (b) regulating the volume of alkaline stripping solution employed relative to the volume of aqueous fluid treated so that the total phenolic compound concentration in the alkaline stripping solution, comprising the sum of the dissociated and unassociated phenolic compound concentrations, is above the solubility of the phenolic compound in water; (c) regulating the pH of the alkaline stripping solution in contact with the membrane to a value at least 0.5 pH units above the acidic dissociation constant of the phenolic compound; (d) adjusting the pH of the phenolic compound containing alkaline stripping solution to a value below the acidic dissociation constant of the phenolic compound and (e) separating the resulting phenolic compound rich phase and the acidified stripping solution.

In a further aspect the present invention provides a process for removing and recovering one or more unassociated phenolic compounds dissolved in aqueous fluid, the process comprising the steps of: (a) transferring the unassociated phenolic compound from the aqueous fluid to an alkaline stripping solution, wherein transfer of the unassociated phenolic compound from the aqueous fluid to the alkaline stripping solution occurs across a membrane; wherein the membrane is a non porous, selectively permeable membrane; (b) regulating the volume of alkaline stripping solution employed relative to the volume of aqueous fluid treated so that the total phenolic compound concentration in the alkaline stripping solution, comprising the sum of the dissociated and unassociated phenolic compound concentrations, is above the solubility of the phenolic compound in the acidified stripping solution of step (d) and no greater than the solubility of the phenolic compound in water: (c) regulating the pH of the alkaline stripping solution in contact with the membrane to a value at least 0.5 pH units above the acidic dissociation constant of the phenolic compound; (d) adjusting the pH of the phenolic compound containing alkaline stripping solution to a value below the acidic dissociation constant of the phenolic compound and (e) separating the resulting phenolic compound rich phase and the acidified stripping solution.

Preferably the aqueous fluid is an aqueous process stream.

Preferably the aqueous fluid is contacted with one side of the membrane and wherein the alkaline stripping solution is contacted with the other side of the membrane. In a more preferred aspect prior to adjusting the pH of the phenolic compound containing alkaline stripping solution, the alkaline stripping solution is removed from contact with the membrane.

Preferably the alkaline stripping solution separated in step (e) is recycled to the aqueous fluid prior to contact with the membrane. In one preferred alternative the alkaline stripping solution separated in step (e) is recycled to the phenolic compound containing alkaline stripping solution prior to removing the alkaline stripping solution from contact with the membrane.

The resulting phenolic compound rich phase of step (e) may be a liquid or a solid.

The membrane of the present invention can be configured in accordance with any of the designs known to those skilled in the art, such as spiral wound, plate and frame, shell and tube, and derivative designs thereof The membranes may be of cylindrical or planar geometry.

For shell and tube designs, the membrane comprises one or more tubular membranes. In this aspect either the aqueous fluid or the alkaline stripping solution is held within the internal volume of the tubular membrane(s) and the other of the aqueous fluid or the alkaline stripping solution is in contact with the external surface of the tubular membrane(s). For spiral wound designs, either the aqueous fluid or the alkaline stripping solution is within the membrane leaves and the other of the aqueous fluid or the alkaline stripping solution is in contact with the external surface of the membrane leaves.

It will appreciated that in an industrial setting preferably the aqueous fluid is held within the internal volume of the tubular membrane(s) and the alkaline stripping solution is in contact with the external surface of the tubular membrane(s), and wherein the tubular membrane(s) and the alkaline stripping solution are operably contained.

In yet further industrial settings preferably the alkaline stripping solution is held within the internal volume of the tubular membrane(s) and the aqueous fluid is in contact with the external surface of the tubular membrane(s), and wherein the tubular membranes and the alkaline stripping solution are operably contained.

The membrane of the present invention is formed from or comprises a material suitable to provide a non-porous, selectively permeable membrane. The membrane may consist of a homogeneous membrane such as a tube or sheet of material, or a composite membrane. The composite membrane may comprise a non-porous, selectively permeable layer and one or more further materials or may comprise a mixture of materials. The non-porous, selectively permeable layer or material prevents direct contact of the aqueous stream with the alkaline stripping solution. This is important. If a direct contact stripping device such as a packed or plate column or microporous membrane contactor is used, the two streams would mix and there would be no resulting separation.

In a preferred aspect the membrane or the non-porous, selectively permeable layer thereof is formed from or comprises a material selected from modified polysiloxane based elastomers including polydimethylsiloxane (PDMS) based elastomers, ethylene-propylene diene (EPDM) based elastomers polynorbomene based elastomers, polyoctenamer based elastomers, polyurethane based elastomers, butadiene and nitrile butadiene rubber based elastomers, natural rubber, butyl rubber based elastomers, polychloroprene (Neoprene) based elastomers, epichlorohydrin elastomers, polyacrylate elastomers, polyethylene, polypropylene, polytetrafluoroethylene (PTFE), polyvinylidene difluoride (PVDF) based elastomers, and mixtures thereof In a preferred aspect the membrane comprises a reinforcing material selected from an external mesh and support. This is particularly advantageous for homogenous tubes or sheets. Such tubes or sheets may be reinforced to increase their burst pressure, for example by overbraiding tubes using fibres of metal or plastic, or by providing a supporting mesh for flat sheets.

When the membrane comprises a non-porous layer and an additional component, the additional component may be a supporting layer. The supporting layer may be a porous support layer. Suitable materials for the open porous support structure are well known to those skilled in the art of membrane processing. Preferably the porous support is formed from or comprises a material selected from polymeric material suitable for fabricating microfiltration, ultrafiltration, nanofiltration or reverse osmosis membranes, including polyethylene, polypropylene, polytetrafluoroethylene (PTFE), polyvinylidene difluoride (PVDF) polyethersulfone, and mixtures thereof Preferably the tubular membranes have a high length to diameter ratios for example the tubular membranes may have internal diameters from 0.5 to 5.0 mm, and/or a wall thicknesses between 0.1 and 1.0 mm and/or a length of from 50 to 500 meters. The length to diameter ratio of the tubular membrane may be from $1 \times 10^4$ to $1 \times 10^6$.

High length to diameter ratio such a those given above are considerably longer than the length to diameter ratios of membranes typically applied in prior art membrane extraction processes, and have the advantage that the aqueous fluid entering the membrane tubes passes down a long flow path before emerging from the membrane. Thus it is possible to remove a high percentage of the phenolic compound contaminants in one pass down a single membrane tube, and this reduces the need for extensive manifolding which arises when the aqueous fluid must be passed through several or many membrane modules to achieve the desired degree of removal. This reduction in manifolding results in cost advantages over shorter membrane tubes.

In a further preferred aspect of the present invention a pH control system is used to regulate the flow of alkaline stripping solution which contacts the membrane.

Control of pH in the alkaline stripping solution is important. Upon contact with the membrane the alkaline stripping solution pH will tend to be decreased by the dissociation of the phenolic compound, and it is advantageous for the process efficiency that the pH of the alkaline stripping solution is kept at least 0.5 pH units above the pKa of the phenolic compound. This may be achieved by fixing the flowrate and strength of the alkaline stripping solution so as to ensure that this condition is always met. A higher alkali concentration in the alkaline stripping solution for given volumes or flows of aqueous fluid and alkaline stripping solution will meet this condition better than a lower concentration of alkali. A higher alkali concentration also makes possible a lower alkali flowrate for a given phenolic compound loading in the aqueous fluid, this results in a lower recycle stream flowrate from step (e), and hence a more cost effective system However use of excessive alkali in the alkaline stripping solution will require excess acid in the recovery stage.

Phenolic compounds are known to form two phase mixtures with water, where one phase is a phenolic compound rich phase, and the other phase is a water rich phase. For example "Solubilities of Organic Compounds" Volume II p 373 by A. Seidell, third edition, Van Nostrand Company, New York 1941 provides data showing that at 30° C. phenol and water can exist as a phenol rich phase comprising 70 wt % phenol and a water rich phase comprising 91 wt % water.

High ionic strength in the aqueous phase serves to reduce the concentration of water in the phenolic compound rich phase and also reduces the concentration of phenolic compound in the aqueous phase, relative to the levels in a pure water—phenolic compound system. In the present invention, all other things being equal, the use of higher alkali concentration in the stripping solution, and the use of a higher acid concentration in the acid solution lead to a higher ionic strength in the acidified stripping solution from step (d), and so to a higher percentage of phenol recovered in the phenol rich phase and to a lower concentration of phenol in the acidified stripping solution which is recycled to the process. Hence in one preferred embodiment of the present invention the alkali concentration in the stripping solution and the acid concentration in the acid solution are as high as possible without causing loss of selective permeability of the membrane through chemical attack.

Preferably, the alkali concentration in the stripping solution and the acid concentration in the acid solution are such that acidified stripping solution separated from the phenolic compound rich phase has a salt concentration of greater than 5 wt %, preferably greater than 10 wt %, preferably greater than 20 wt % and preferably greater than 25 wt %.

Preferably the stripping solution in contact with the nonporous membrane is well mixed so that its composition is well mixed throughout the volume operably in contact with the nonporous membrane.

Preferably the pH of the alkaline stripping solution in contact with the non-porous membrane is controlled so that it is substantially the same throughout the alkaline stripping solution in contact with the non-porous membrane separating layer.

Preferably the aqueous fluid contains a phenolic compound selected from phenol, cresols, chlorophenols, dichlorophenols, dimethylphenols, nitrophenols, bromophenols, chlorocresols, benzenediols, benzoquinones, and mixtures thereof Preferably the alkaline stripping solution comprises a mineral alkali selected from sodium hydroxide, potassium hydroxide, calcium hydroxide, and mixtures thereof Preferably the pH of the phenolic compound containing alkaline stripping solution is adjusted in step (d) by the addition of an acid.

Preferably the acid is an aqueous solution of an acid selected from hydrochloric acid, sulphuric acid, nitric acid, phosphoric acid, and mixtures thereof In a further preferred aspect the aqueous fluid is contacted with one side of a plurality of membranes in series, in parallel or in a combination thereof, and wherein the alkaline stripping solution is contacted with the other side of each of the plurality of membranes.

In further preferred aspect contact between the alkaline stripping solution and molecular oxygen is partially, substantially or completely prevented. This aspect is advantageous because yield of phenolic compounds is improved during the recovery stages (d) and (e) of the process. Without being bound by theory, it is believed that this is due to oxidation reactions of the phenate ion which occur under alkaline conditions in the presence of molecular oxygen (see for example "Recovery process for phenolic compounds from coal-derived oils by ions of soluble metal salts" Ge Y. and Jin, H. FUEL 1996 Volume 75 Number 14 pages 1681–1683). Preferably, exposure of the alkaline stripping solution to molecular oxygen can be limited or prevented by careful construction and operation of the process equipment employed, so that vessels for the stripping solution and/or wastewater are operated full of liquid and with no gaseous headspace. Preferably, exposure of the alkaline stripping solution to molecular oxygen can be limited or prevented by nitrogen sparging of the stripping solution and/or the gas headspace above the stripping solution, and/or by inert gas, preferably nitrogen, sparging of the wastewater and/or the gas headspace above the wastewater. By the term "inert gas" it is preferably meant a gas containing oxygen at levels below 1 wt. %.

The process may be performed in a continuous, semi-continuous or discontinuous (batch mode) manner. In the latter aspect the flow of at least one of the aqueous fluid, the alkaline stripping solution, and the alkali solution is discontinuous.

In one aspect the resulting phenolic compound rich phase of step (e) is contacted with an organic solvent and subsequently treated in a further process. In this aspect it may be desirable to contact the phenolic compound containing alkaline stripping solution and/or the separated phenolic compound rich phase with a solvent or solvent mixture in step (e). This may be particularly useful when the separated phenolic compound rich phase is a solid. The solvent introduced may dissolve the solid. This may be further useful when this solid is a product or reactant in a reaction and where the solid and the solvent used to dissolve the solid can be sent to the further process in which the solid material is produced or consumed.

The process of the present invention may be performed in a reactor comprising at least a first zone, a second zone, a third zone, and a fourth zone; wherein each of the zones is discrete from each other zone; wherein the first zone and the second zone are separated by the non porous membrane; wherein the first zone contains the aqueous fluid; wherein the second zone and fourth zone contain the alkaline stripping solution; wherein the third zone contains phenolic compound containing alkaline stripping solution; wherein the third zone and the fourth zone are operably connected to each other; wherein the second zone is operably connected to the fourth zone; and wherein the alkaline stripping solution is circulated between the fourth zone and the second zone such that the alkaline stripping solution is well mixed throughout its volume.

Preferably, the alkaline stripping solution is circulated between the fourth zone and the second zone at a high rate relative to the flow of aqueous fluid. By the term "high rate" it is preferably meant that the volume of alkaline stripping solution contacted with the membrane is greater than the volume of aqueous fluid contacted with the membrane. The ratio of alkaline stripping solution volume to aqueous fluid volume contacted with the membrane may be >2:1, >5:1, or >10:1. A pH control system may be used to regulate the flow of alkaline stripping solution between the fourth zone and the second zone.

The aqueous fluid and/or the alkaline stripping solution of the present invention may be heated before or during contact with the membrane. The aqueous fluid and/or the alkaline stripping solution of the present invention may have a temperature above room temperature (25° C.). This may increase the rate of mass transfer across the non-porous membrane. In a further preferred embodiment, the temperature of the aqueous fluid and/or the alkaline stripping solution may be above 60° C. In yet a further preferred embodiment, the temperature of the aqueous fluid and/or the alkaline stripping solution may be above 70° C.

It is known as for example in "Solubilities of Organic Compounds" Volume II p 373 by A. Seidell, third edition, Van Nostrand Company, New York 1941 that at temperatures above 65° C. phenol and water can be totally miscible. In the present invention, temperatures may rise above ambient upon addition of mineral acid to the alkaline stripping solution in step (d), or they may be deliberately raised to increase mass transfer of the phenolic compound in step (a). In one preferred embodiment, the alkaline stripping solution from step (d) is cooled prior to step (e) to effect an improved separation of the phenolic compound rich phase and the acidified stripping solution.

In a further preferred aspect the aqueous fluid contains substantial quantities of dissolved inorganic or organic materials. By the term "substantial quantities" it is meant greater than 0.1 wt %. The inorganic materials may include salts, such as sodium chloride, potassium chloride and mixtures thereof The organic materials may include solvents, such as methanol, ethanol, acetone, acetate and mixtures thereof The phenolic compound in the alkaline stripping solution dissociates according to an equilibrium reaction described by equation (1). Even at high pH, there will be some finite fraction of the phenolic compound present in unassociated form, and the total phenolic compound concentration will be equal to the sum of the concentration of dissociated and the concentration of unassociated phenolic compound. In general, the higher the concentration of total phenolic compound in the alkaline stripping solution at a given pH, the higher will be the concentration of unassociated phenolic compound. This unassociated phenolic compound will act to reduce the driving force for mass transfer of unassociated phenolic compound from the aqueous fluid to the alkaline stripping solution.

This effect will be relatively greater for the aqueous fluid in the section of membrane near the point of exit of the aqueous fluid from the membrane.

Thus in a further preferred embodiment of the present invention, it is desirable to use two well mixed stripping stages in series. In this embodiment, the aqueous fluid first contacts a membrane whose other side is in contact with a well mixed strength 1 alkaline stripping solution in a first stripping stage, and then contacts a second membrane whose other side is in contact with a well mixed strength 2 alkaline stripping solution in a second stage. Strength of an alkaline stripping solution is determined by the strength of the alkali, for example, the mineral alkali, fed to the alkaline stripping solution. In this aspect, the mineral alkali concentration fed to stripping solution 1 is stronger than the mineral alkali concentration fed to stripping solution 2. The aqueous fluid passes from the membrane of stripping stage 1 to the membrane of stripping stage 2. Mineral alkali is fed to the alkaline stripping solution in stripping stage 2, and the resulting strength 2 stripping solution from stage 2 is passed into stage 1 where further mineral alkali is added to increase the strength of the alkaline stripping solution in stage 1 to strength 1. The total phenolic compound concentration in stage 1 is greater than the total phenolic compound concentration in stage 2. The pH may be controlled to be constant in each stripping stage and may be set at different values in stage 1 and stage 2. The use of more than two stages is also envisaged.

The invention will now be described, by way of example only, with reference to the accompanying drawings, in which:

FIG. 1 is a schematic of an apparatus operating the process of the present invention.

FIG. 2 is a schematic of an apparatus operating the process of the present invention.

FIG. 3 is a schematic of an apparatus operating the process of the present invention.

FIG. 4 is a schematic of an apparatus operating the process of the present invention.

FIG. 5 is a schematic of an apparatus operating the process of the present invention.

FIG. 6 is a schematic of an apparatus operating the process of the present invention.

FIG. 7 is a schematic of an apparatus operating the process of the present invention.

FIG. 1 shows a schematic of one embodiment of the process. The aqueous fluid containing unassociated phenolic compounds (1) passes on one surface of a membrane containing at least one non-porous separating layer (5), optionally mounted in a membrane module (6). Unassociated phenolic compounds in the wastewater permeate across the membrane into the alkaline stripping solution (3), whose pH is such that the phenolic compounds are converted into their corresponding salts. The aqueous fluid exiting the membrane has a reduced concentration of phenolic compounds relative to the aqueous fluid (1) entering the membrane. The phenolic compound laden alkaline stripping solution (4) leaves the membrane module (6) containing dissociated phenolic compounds and enters a neutralisation vessel (7). By manipulation of the ratio between the volume of aqueous stream fed (1) and volume of alkaline stripping solution fed (3), i.e. by using a ratio greater than 1, the concentration of dissociated phenolic compounds in the phenolic compound laden alkaline stripping solution (4) is elevated to levels higher than the saturation concentration of unassociated phenolic compounds in water. In the neutralisation vessel (7) a mineral acid (8) is added to adjust pH of the solution to a value below the pKa of the phenolic compound. This converts the phenolic compound back to an unassociated form Since it is at a concentration higher than the saturation concentration of unassociated phenolic compound in water, the phenolic compound precipitates out of the aqueous solution as a phenolic compound rich liquid or solid. The neutralisation vessel (7) may be optionally stirred. The resulting two phase mixture (9) is passed to a settling vessel (10) where the two phases are separated. The organic rich phase (either liquid or solid) is removed (11) from the settling vessel (10), and the phenolic compound saturated aqueous layer (12) is recirculated back either to the aqueous process stream (1), or to the neutralisation tank (7).

In a preferred embodiment, the membranes may comprise a bundle of tubular membranes with suitable head piece connections for allowing flow of the aqueous fluid to pass through the interior of the membranes. This bundle of tubular membranes may be suspended in a tank or other vessel so that the outside surface of the fibres is substantially immersed in the alkaline stripping solution. In this case the alkaline stripping solution will be mixed or agitated using a stirrer or pump or some other suitable device to ensure that the alkaline stripping solution is well mixed at all times and the composition of the stripping solution in contact with the membrane will be the same as the concentration of the stripping solution (4) leaving the tank (15). FIG. 2 shows this general arrangement where a bundle of tubular membranes (13) are connected at each end to allow wastewater flow through headpieces (14), and are immersed in a tank (15) of alkaline stripping solution.

FIG. 3 shows yet another preferred embodiment, in which one or more elastomeric tubular membranes (16) connected using suitable headpieces (17) are suspended in a well mixed tank (15) containing alkaline stripping solution (4). The elastomeric tubular membranes can be coiled, stacked or otherwise arranged in the tank so that they have their surfaces substantially immersed in the alkaline stripping solution (4). It is advantageous in this embodiment to use elastomeric tubular membranes which have high length to diameter ratios for example the elastomeric tubular membranes might have internal diameters from 0.5 to 5.0 mm, wall thicknesses between 0.1 and 1.0 mm and lengths from 50 to 500 meters, i.e. length to diameter ratios of $1 \times 10^4$ to $1 \times 10^6$.

The configurations illustrated in FIGS. 2 and 3 are made possible by the rapid dissociation reaction in the alkaline stripping solution which removes the need to configure the flow over the outside surfaces of the membrane so as to provide high rates of film mass transfer.

It is apparent to one skilled in the art that it is desirable to use a high concentration alkali (by way of non limiting example, sodium hydroxide above 20 wt. % NaOH), as a feed alkaline stripping solution (3), while maintaining pH in the alkaline stripping solution in contact with the non-porous membrane (4) separating layer at a high enough value to minimise the need for alkali addition and to ensure maximal lifetime of the non-porous membrane separating layer. It is with these objectives in mind that the configurations of FIGS. 2, 3, 4 and 5 are found to have advantages over passing the aqueous and organic streams in countercurrent flow through membrane modules as shown in FIG. 1. In the configurations of FIGS. 2, 3, 4 and 5 the alkali added (3) can be concentrated but as it is immediately mixed into the phenolic compound laden alkaline stripping solution (4) in the well mixed tank (15) the actual alkali concentration of the alkaline stripping solution in contact with the non-porous membrane separating layers can be everywhere substantially less than the alkali concentration of the feed alkaline stripping solution (3).

A further preferred embodiment of the process as shown in FIG. 4 by way of non-limiting example can be employed. A well mixed tank (15) containing an elastomeric membrane tube (16) immersed in alkaline stripping solution (4) has a pH sensor (18) in contact with the well mixed alkaline stripping solution (4). This pH sensor measures pH and transmits this information to a control device (19) which regulates flow of feed alkaline stripping solution (3) to the tank to hold pH at the desired value. Using this approach pH in the tank (15) can be controlled to the lowest value consistent with good process efficiency, thus minimising alkali concentration in the tank and in the phenolic compound laden alkaline stripping solution (4). This has consequent advantages for neutralisation costs and membrane lifetime.

In yet another preferred embodiment, shown in FIG. 5, the advantages of a well mixed alkaline stripping solution in a remote stripping tank (20) are shown in connection with the use of a membrane module of the type used in FIG. 1. The pH is controlled in the stripping tank by a pH sensor (18) and a control device (19) which regulates the flow feed alkaline stripping solution (3) to the stripping tank (20). The alkaline stripping solution is recirculated (21) to the membrane module or modules at a high rate so that for all practical purposes the alkaline stripping solution can be considered well mixed throughout its volume. Phenolic compound laden alkaline stripping solution (4) is withdrawn and passed to the neutralisation tank (7).

In yet another preferred embodiment the temperature of the alkaline stripping solution in tank (15) or tank (20) and or the aqueous stream (1) can be increased above ambient conditions to increase the rate of mass transfer across the non-porous separating layer of the membrane.

In yet another preferred embodiment shown in FIG. 6, the use of two stripping stages is shown with two strengths of alkaline stripping solution. The aqueous fluid (1) enters the first stripping stage in which a membrane (30) is suspended in the first stage tank (31). An alkaline stripping solution containing mineral alkali (32) is added to the stage 1 tank (31) automatically by a pH controller (34) connected to a pH probe (33). The stripping solution in stage 1 is well mixed throughout the volume of the stage 1 tank (31) so that it is of identical composition to the stripping solution (42) exiting the stage 1 tank. The aqueous fluid (35) flows out of stage 1 and into stage 2 where a second membrane (40) is suspended in the stage 2 tank (41). The aqueous fluid (2) flows out of the second membrane (40) with a reduced concentration of phenolic compound relative to stream (1). In the second stage, alkaline stripping solution containing mineral alkali (37) at a lower concentration than stream (32) is added to the stage 2 tank (41) automatically by a pH controller (39) connected to a pH probe (38). The stripping solution in the stage 2 tank (41) is well mixed throughout the volume of the stage 2 tank so that it is of identical composition to the stripping solution (36) exiting the stage 2 tank. The stripping solution (36) exiting the stage 2 tank (41) is fed to the stage 1 tank (31). The system is configured and operated so that the total phenolic compound concentration in stream (36) is less than the total phenolic compound concentration in stream (42). The stripping solution (42) from the stage (1) tank is passed to the neutralisation vessel (7). Following phase separation, the phenolic compound saturated aqueous layer (12) is recirculated back to the aqueous fluid (1).

In yet another preferred embodiment shown in FIG. 7, the process of FIG. 4 has a nitrogen sparge added to the stripping solution (4) in the well mixed tank (15) to avoid contact between the stripping solution and molecular oxygen. A stream of nitrogen (50) is introduced to the well mixed tank (15) containing the stripping solution (4), at a point below the stripping solution liquid level. The nitrogen rises through the stripping solution, sweeps the gas headspace in the vessel, and leaves at the top of the vessel (51). The processes described above may be operated continuously, semi-continuously or in batch mode. The tanks may be single tanks or multiple tanks. The neutralisation vessel (7) and the phase separating vessel (10) may be combined into the same vessel. Mixing of one or all of the tanks may be achieved by using any device known to those skilled in the art, such as mixers, pumps, or air lift devices. Variations and changes may be made by those skilled in the art without departing from the spirit of the invention.

The invention will now be described in further detail in the following non-limiting Examples.

EXAMPLES

Example 1

The following example describes batch operation of the present invention. 1000 mL of alkaline stripping solution comprising a 30% solution of sodium hydroxide were added to a stirred tank containing a 25 meter length of a silicone rubber membrane tube with internal diameter of 3 mm, wall thickness 0.5 mm 20 liters of a wastewater containing 5 wt. % phenol were recirculated from a drum through the inside of the elastomeric membrane tube. 20% sodium hydroxide was added regularly to the alkaline stripping solution to maintain pH greater than 12. After 25 days the experiment was stopped, and the alkaline stripping solution removed. The pH of the alkaline stripping solution was adjusted to 1 by addition of 33 wt. % HCl solution, and a pinkish colored organic layer formed and was separated from the aqueous phase. This organic liquid was analysed via gas chromatography and found to be more than 60 wt % phenol.

Example 2

The following example describes continuous operation of the present invention. 1000 mL of alkaline stripping solution were added to a stirred tank containing a 25 meter length of a silicone rubber membrane tube with internal diameter of 3 mm, wall thickness 0.5 mm. A pH sensor was suspended in the tank and a controller was connected to the sensor so as to add 30 wt. % sodium hydroxide to the tank when required to maintain pH. The controller held pH at 13+/−0.2 pH units. A flow of aqueous process stream containing phenol at 5 wt. % was pumped from a drum and passed through the inside of the membrane tube. The overflow of the alkaline stripping solution was periodically removed to a tank where pH was adjusted, resulting in formation of a pinkish coloured organic liquid. The resulting aqueous and organic phases were separated and the aqueous phase mixed with the aqueous process stream in the drum. The pinkish coloured organic liquid was analysed and found to be greater than 60 wt % phenol.

Example 3

The following example describes the use of the claimed process in batch mode to recover phenolic compounds from a wastewater. A wastewater stream from phenoxy acid manufacture was treated. The wastewater had a pH of 0.85 and contained ortho-cresol (OC), ortho-chloro-ortho-cresol (OCOC), and para-chloro-ortho-cresol (PCOC). The waste was neutralised to a pH around 5.5 with 47 wt % NaOH prior to extraction of cresols 10 liters of aqueous waste were used in the test. This was recirculated through 37 m of a 3 mm i.d.×0.5 mm wall thickness silicone rubber membrane tube immersed in 1.2 liters of a caustic stripping solution. There was a gas headspace present above the liquids in the vessels used to hold both the wastewater and the stripping solution. The headspace of both vessels was continuously fed with nitrogen gas to maintain a nitrogen blanket over the liquids. The stripping solution was initially a dilute caustic solution at pH 12, and 47% NaOH was added over time via a pH controller to maintain the pH at 12 as cresols crossed the membrane. The experiment was conducted at 30° C. During the extraction test essentially all the cresols (as identified by GC analysis) were removed from the wastewater, and the Total Organic Carbon (TOC) of the wastewater was reduced by over 90%.

Concentrations of cresols in the wastewater were determined by extraction of aqueous samples using dichloromethane and subsequent injection onto a gas chromatograph (GC). An organic rich phase was recovered from the wastewater via the claimed process following pH adjustment of the stripping solution to acid conditions with 37% HCl. Purity of the recovered organics was assessed by adding a drop of the recovered organic phase to dichloromethane and injecting onto the GC. The relative fractions of the three cresols in the recovered organic phase (determined by GC analysis) were 21% OC, 50% OCOC and 29% PCOC.

Example 4

A wastewater containing 2,4 dichlorophenol (24DCP) was treated using the claimed process in batch mode. The membrane was as described in example 3, and a nitrogen blanket was used as in example 3. The 24DCP containing wastewater had a pH of 10 and contained 24DCP, phenoxy butyric acid, n-butanol, butyrolactone, and 4-hydroxy butyric acid. During the extraction test essentially all the 24DCP (as identified by GC analysis) was removed from the wastewater, and the Total Organic Carbon (TOC) of the waste was reduced by around 35%. The stripping solution was initially a dilute caustic solution at pH 12, and 47% NaOH was added over time via a pH controller to maintain the pH at 12 as phenolics crossed the membrane. The experiment was conducted at 30° C. Following removal of the phenolic compounds, pH of the stripping solution was adjusted to acid conditions with 37% HCl. 8 liters of aqueous phase were processed in a laboratory rig, producing 21 mLs of recovered organic phase, which turned solid overnight. Dissolution of a drop of this recovered organic in dichloromethane, followed by GC analysis, using peak area as a proxy for quantity, showed this organic material to be 98% 24DCP.

Example 5

A wastewater containing para-chloro-ortho-cresol (PCOC) was treated using batch operation of the claimed process. The membrane was as described in example 3, and a nitrogen blanket was used as in example 3. The PCOC wastewater had a pH of 1.1 and contained PCOC, phenoxy butyric acid, butyrolactone, and 4-hydroxy butyric acid. The pH of the waste was adjusted to 2.5 before extraction using 47 wt % NaOH. During the extraction test over 95% of the PCOC (as identified by GC analysis) was removed from the wastewater, and the Total Organic Carbon (TOC) of the waste was reduced by around 50%. The stripping solution was initially a dilute caustic solution at pH 12, and 47% NaOH was added over time via a pH controller to maintain the pH at 12 as phenolics crossed the membrane. The experiment was conducted at 30° C. Following removal of the phenolic compounds, pH of the stripping solution was adjusted to acid conditions with 37% HCl. 10 liters of aqueous phase were processed in a laboratory rig, producing 19 mLs of recovered organic phase, which remained as a liquid. Dissolution of a drop of this recovered organic phase in dichloromethane, followed by GC analysis, using peak area as a proxy for quantity, showed this organic material to be 96% PCOC.

Example 6

A wastewater containing phenol was treated using batch operation of the claimed process. The membrane was as described in example 3, and a nitrogen blanket was used as in example 3. The wastewater had a pH of between 2.5 and 3.5, and contained 7.2 g $L^{-1}$ phenol. During the extraction test over 99% of the phenol (as identified by GC analysis) was removed from the wastewater, and the Total Organic Carbon (TOC) of the waste was reduced by around 85%. The stripping solution was initially a dilute caustic solution at pH 12, and 47% NaOH was added over time via a pH controller to maintain the pH at 12 as phenol crossed the membrane. The experiment was conducted at 30° C. Following removal of the phenol, pH of the stripping solution was adjusted to acid conditions with 37% HCl. 20 liters of aqueous phase were processed in a laboratory rig, producing 110 mLs of recovered organic-rich phase, which remained as a liquid. Dissolution of a drop of this recovered organic-rich phase in dichloromethane, followed by GC analysis, using peak area as a proxy for quantity, showed the organic material present to be 100% phenol.

Example 7

A wastewater containing cresols was treated using batch operation of the claimed process. Three distinct organic compounds were detected in the wastewater by gas chromatography (GC) using extraction into dichloromethane followed by injection onto a column and detection with FID. One of these was identified as p-cresol while the other two (henceforth compounds A and B), which had lower retention times in the GC method used (p-cresol 6.30 minutes; compound A 5.95 minutes; compound B 5.00 minutes) were not identified. The relative fractions of the organic compounds in the wastewater was approximately 67% p-cresol, 22% compound A and 11% compound B. The membrane was as described in example 3, and a nitrogen blanket was used as in example 3.

The wastewater had a pH of between 9–10. The stripping solution was initially a dilute caustic solution at pH 12, and 47% NaOH was added over time via a pH controller to maintain the pH at 12 as phenolics crossed the membrane. The experiment was conducted at 30° C. Following removal of the phenolic compounds, pH of the stripping solution was adjusted to acid conditions with 37% HCl. 10 liters of aqueous phase were processed in a laboratory rig, producing 150 mLs of recovered organic phase, which remained as a liquid. The recovered organic phase contained approximately 10% water. The relative fractions of the three organic compounds in the recovered organic phase (determined by GC analysis) were 66% p-cresol, 26% compound A and 6% compound B.

Example 8

The following example describes batch operation of the present invention with the alkaline stripping solution in contact with the internal surface of a tubular membrane and the wastewater in contact with the external surface of the tubular membrane. 75 L of wastewater containing 2 wt. % phenol were added to a stirred tank containing a 100 meter length of a silicone rubber membrane tube with internal diameter of 3 mm, wall thickness 0.5 mm. 2 liters of an alkaline stripping solution comprising a 10 wt % solution of sodium hydroxide was recirculated from a container through the inside of the elastomeric membrane tube and back to the container. Temperature of the wastewater was controlled at 50° C. Nitrogen was sparged through the wastewater tank and the alkaline stripping solution container. After 36 hours the experiment was stopped, and the alkaline stripping solution removed. The pH of the alkaline stripping solution was adjusted to less than 5 by addition of 33 wt. % HCl solution, and a pinkish coloured organic layer formed and was separated from the aqueous phase. This organic liquid was analysed via gas chromatography and found to be more than 60 wt % phenol.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry or related fields are intended to be within the scope of the following claims.

What is claimed is:

1. A process for removing and recovering one or more unassociated phenolic compounds dissolved in aqueous fluid, the process comprising the steps of
   (a) transferring the one or more unassociated phenolic compounds from the aqueous fluid to an alkaline stripping solution, wherein transfer of the one or more unassociated phenolic compounds from the aqueous fluid to the alkaline stripping solution occurs across a membrane; wherein the membrane is a non porous, selectively permeable membrane;
   (b) regulating the volume of alkaline stripping solution employed relative to the volume of aqueous fluid treated so that the total phenolic compound concentration in the alkaline stripping solution, comprising the sum of the dissociated and unassociated phenolic compound concentrations, is above the solubility of the phenolic compounds in the acidified stripping solution of step (d);
   (c) regulating the pH of the alkaline stripping solution in contact with the membrane to a value at least 0.5 pH units above the acidic dissociation constant of the phenolic compound;
   (d) adjusting the pH of the phenolic compound containing alkaline stripping solution to a value below the acidic dissociation constant of the phenolic compound and;
   (e) separating the resulting phenolic compound rich phase and the acidified stripping solution.

2. A process according to claim 1 wherein step (b) comprises regulating the volume of alkaline stripping solution employed relative to the volume of aqueous fluid treated so that the total phenolic compound concentration in the alkaline stripping solution is above the solubility of the phenolic compounds in water.

3. A process according to claim 1 wherein the aqueous fluid is an aqueous process stream.

4. A process according to claim 1 wherein the aqueous fluid is contacted with one side of the membrane and wherein the alkaline stripping solution is contacted with the other side of the membrane.

5. A process according to claim 4 wherein prior to adjusting the pH of the phenolic compound containing alkaline stripping solution, the alkaline stripping solution is removed from contact with the membrane.

6. A process according to claim 4 wherein the acidified stripping solution separated in step (e) is recycled to the aqueous fluid prior to contact with the membrane.

7. A process according to claim 5 wherein the alkaline stripping solution separated in step (e) is recycled to the phenolic compound containing alkaline stripping solution prior to removing the alkaline stripping solution from contact with the membrane.

8. A process according to claim 1 wherein the resulting phenolic compound rich phase of step (e) is a liquid.

9. A process according to claim 1 wherein the resulting phenolic compound rich phase of step (e) is a solid.

10. A process according to claim 1 wherein the membrane is mounted in a plate and frame configuration, a shell and tube configuration, or a spiral wound configuration.

11. A process according to claim 1 wherein the membrane comprises one or more tubular membranes and either the aqueous fluid or the alkaline stripping solution is held within the internal volume of the tubular membrane(s) and the other of the aqueous fluid or the alkaline stripping solution is in contact with the external surface of the tubular membrane(s).

12. A process according to claim 11 wherein the aqueous fluid is held within the internal volume of the tubular membrane(s) and the alkaline stripping solution is in contact with the external surface of the tubular membrane(s), and wherein the tubular membrane(s) and the alkaline stripping solution are operably contained.

13. A process according to claim 11 wherein the alkaline stripping solution is held within the internal volume of the tubular membrane(s) and the aqueous fluid is in contact with the external surface of the tubular membrane(s), and wherein the tubular membrane(s) and the aqueous fluid are operably contained.

14. A process according to claim 1 wherein the tubular membrane(s) is elastomeric.

15. A process according to claim 1 wherein the tubular membrane(s) has a length to diameter ratio of from 10,000 to 1,000,000.

16. A process according to claim 1 wherein the alkaline stripping solution in contact with the nonporous membrane is well mixed throughout its volume such that its composition is uniform throughout.

17. A process according to claim 1 wherein the pH of the alkaline stripping solution in contact with the non-porous membrane is controlled so that it is substantially the same throughout the volume of alkaline stripping solution in contact with the non-porous membrane separating layer.

18. A process according to claim 1 wherein the aqueous fluid contains a phenolic compound selected from phenol, cresols, chlorophenols, dichlorophenols, chlorocresols, dimethylphenols, nitrophenols, bromophenols, benzenediols, benzoquinones, and mixtures thereof.

19. A process according to claim 1 wherein the alkaline stripping solution comprises a mineral alkali selected from sodium hydroxide, potassium hydroxide, calcium hydroxide, and mixtures thereof.

20. A process according to claim 1 wherein the pH of the phenolic compound containing alkaline stripping solution is adjusted in step (d) by the addition of an acid.

21. A process according to claim 20 wherein the acid is an aqueous solution of an acid selected from hydrochloric acid, sulphuric acid, phosphoric acid, nitric acid, and mixtures thereof.

22. A process according to claim 1 wherein the membrane is formed from or comprises a material selected from modified polysiloxane based elastomers including polydimethylsiloxane (PDMS) based elastomers, ethylene-propylene diene (EPDM) based elastomers, polynorbornene based elastomers, polyoctenamer based elastomers, polyurethane based elastomers, butadiene and nitrile butadiene rubber based elastomers, natural rubber, butyl rubber based elastomers, polychloroprene (Neoprene) based elastomers, epichlorohydrin elastomers, polyacrylate elastomers, polyethylene, polypropylene, polytetrafluoroethylene (PTFE), polyvinylidene difluoride (PVDF) based elastomers, and mixtures thereof.

23. A process according to claim 1 wherein the membrane comprises a reinforcing material selected from an external mesh and support.

24. A process according to claim 1 wherein the membrane is a composite membrane comprising a porous support and at least one non-porous layer.

25. A process according to claim 24 where the porous support is formed from or comprises a material selected from polymeric material suitable for fabricating microfiltration, ultrafiltration, nanofiltration or reverse osmosis membranes, including polyethylene, polypropylene, polytetrafluoroethylene (PTFE), polyvinylidene difluoride (PVDF) polyethersulfone, and mixtures thereof.

26. A process according to claim 1 wherein the aqueous fluid is contacted with one side of a plurality of membranes in series, in parallel or in a combination thereof, and wherein the alkaline stripping solution is contacted with the other side of each of the plurality of membranes.

27. A process according to claim 1 wherein the process is performed in a continuous manner.

28. A process according to claim 21 wherein the flow of at least one of the aqueous fluid, the alkaline stripping solution, and the alkali solution is discontinuous.

29. A process according to claim 1 wherein the resulting phenolic compound rich phase of step (e) is contacted with an organic solvent and subsequently treated in a further process.

30. A process according to claim 1 wherein the process is performed in a reactor comprising at least a first zone, a second zone, a third zone, and a fourth zone;

wherein each of the zones is discrete from each other zone;

wherein the first zone and the second zone are separated by the non porous membrane;

wherein the first zone contains the aqueous fluid;

wherein the second zone and fourth zone contain the alkaline stripping solution;

wherein the third zone contains phenolic compound containing alkaline stripping solution;

wherein the third zone and the fourth zone are operably connected to each other;

wherein the second zone is operably connected to the fourth zone; and wherein the alkaline stripping solution is circulated between the fourth zone and the second zone such that the alkaline stripping solution is well mixed throughout its volume.

31. A process according to claim 30 wherein a pH control system is used to regulate the flow of alkaline stripping solution between the fourth zone and the second zone.

32. A process according to claim 1 wherein at least one of the aqueous fluid and the alkaline stripping solution has a temperature above room temperature.

33. A process according to claim 1 wherein at least one of the aqueous fluid and the alkaline stripping solution has a temperature above 60° C.

34. A process according to claim 1 wherein at least one of the aqueous fluid and the alkaline stripping solution has a temperature above 70° C.

35. A process according to claim 1 wherein the aqueous fluid contains substantial quantities of dissolved inorganic or organic materials.

36. A process according to claim 1 wherein the alkaline stripping solution is cooled prior to step (e) to effect an improved separation of the phenolic compound rich phase and the acidified stripping solution.

37. A process according to claim 1 wherein the acidified stripping solution separated from the phenolic compound rich phase has a salt concentration of greater than 5 wt %.

38. A process according to claim 37 wherein the acidified stripping solution separated from the phenolic compound rich phase has a salt concentration of greater than 10 wt %.

39. A process according to claim 37 wherein the acidified stripping solution separated from the phenolic compound rich phase has a salt concentration of greater than 20 wt %.

40. A process according to claim 1 wherein contact between the alkaline stripping solution and molecular oxygen is partially, substantially or completely prevented.

41. A process according to claim 40 wherein contact between the alkaline stripping solution and molecular oxygen is prevented by sparging any of the alkaline stripping solution, the gas headspace above the alkaline stripping solution, the wastewater, or the gas headspace above the wastewater, with an inert gas.

42. A process according to claim 41 wherein the inert gas is nitrogen.

43. A process according to claim 40 wherein the vessels containing either the stripping solution or the wastewater are maintained full such that there is no gas headspace above the liquids in the vessels and contact between the alkaline stripping solution and molecular oxygen is prevented.

* * * * *